US00PP33980P2

(12) United States Plant Patent
Barnes

(10) Patent No.: US PP33,980 P2
(45) Date of Patent: Mar. 1, 2022

(54) ***CALYLOPHUS* PLANT NAMED 'WNCYLALEM'**

(50) Latin Name: *Calylophus hybrida*
Varietal Denomination: WNCYLALEM

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 17/372,228

(22) Filed: Jul. 9, 2021

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1, 432, 460
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct *Calylophus* plant named 'WNCYLALEM', characterized by its outwardly spreading and mounding to eventually trailing and decumbent plant habit; moderately vigorous to vigorous growth habit and rapid growth rate; freely branching habit; dense and bushy plant form; freely flowering habit; large light yellow-colored flowers that are held above and beyond the foliar plane; and excellent garden performance.

2 Drawing Sheets

Figure 1:
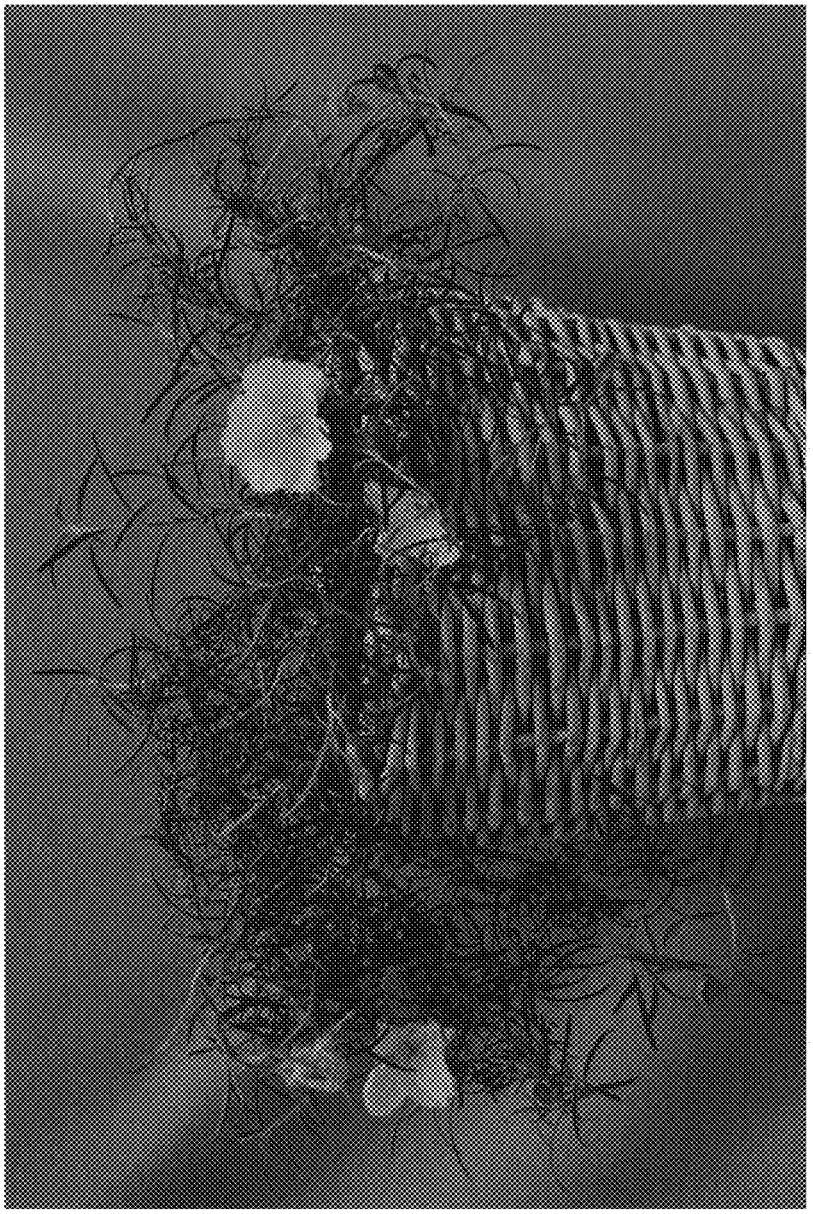

Botanical designation: *Calylophus hybrida.*
Cultivar denomination: 'WNCYLALEM'.

CROSS-REFERENCED TO CLOSELY-RELATED APPLICATIONS

Title: *Calylophus* Plant Named 'WNCYLASUN'
Application Ser. No. 17/371,431
Filed: Concurrently with the instant application

BACKGROUND OF THE INVENTION

The present invention relates to a new and distinct cultivar of *Calylophus* plant, botanically known as *Calylophus hybrida*, commonly referred to as Texas Primrose and hereinafter referred to by the name 'WNCYLALEM'.

The new *Calylophus* plant is a product of a planned breeding program conducted by the Inventor in Bonsall, Calif. The objective of the breeding program is to create new vigorous, freely-branching and uniformly mounding *Calylophus* plants with numerous attractive flowers, long flowering period and good garden performance.

The new *Calylophus* plant originated from a self-pollination made by the Inventor on Apr. 25, 2017 in Bonsall, Calif. of a proprietary selection of *Calylophus hybrida* identified as code number 17TX073-02, not patented. The new *Calylophus* plant was discovered and selected by the Inventor as a single flowering plant within the progeny of the stated self-pollination in a controlled greenhouse environment in Bonsall, Calif. on Sep. 13, 2018.

Asexual reproduction of the new *Calylophus* plant by vegetative terminal cuttings in a controlled greenhouse environment in Bonsall, Calif. since Sep. 18, 2018 has shown that the unique features of this new *Calylophus* plant are stable and reproduced true to type in successive generations.

SUMMARY OF THE INVENTION

Plants of the new *Calylophus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNCYLALEM'. These characteristics in combination distinguish 'WNCYLALEM' as a new and distinct *Calylophus* plant:

1. Outwardly spreading and mounding to eventually trailing and decumbent plant habit.
2. Moderately vigorous to vigorous growth habit and rapid growth rate.
3 Freely branching habit; dense and bushy plant form.
4. Freely flowering habit.
5. Large light yellow-colored flowers that are held above and beyond the foliar plane.
6. Excellent garden performance.

Plants of the new *Calylophus* can be compared to plants of the parent selection. In side-by-side comparisons, plants of the new *Calylophus* differ primarily from plants of the parent selection in the following characteristics:

1. Plants of the new *Calylophus* flower for a longer period of time than plants of the parent selection.
2. Plants of the new *Calylophus* have larger flowers than plants of the parent selection.
3. Flowers of plants of the new *Calylophus* are lighter yellow in color than flowers of plants of the parent selection.

Plants of the new *Calylophus* can be compared to plants of *Calylophus hybrida* 'WNCYLASUN', disclosed in a U.S. Plant Patent application filed concurrently. In side-by-side comparisons, plants of the new *Calylophus* differ primarily from plants of 'WNCYLASUN' in flower color as plants of the new *Calylophus* have lighter yellow-colored flowers than plants of 'WNCYLASUN'.

Plants of the new *Calylophus* can be compared to plants of *Calylophus drummondianus* 'Southern Belle', not patented. In side-by-side comparisons, plants of the new *Calylophus* differ primarily from plants of 'Southern Belle' in the following characteristics:

1. Plants of the new *Calylophus* are more vigorous than plants of 'Southern Belle'.
2. Plants of the new *Calylophus* flower for a longer period of time than plants of 'Southern Belle'.
3. Plants of the new *Calylophus* have larger flowers than plants of 'Southern Belle'.
4. Flowers of plants of the new *Calylophus* are held above and beyond the foliage whereas flowers of plants of 'Southern Belle' are held within the foliar plane.
5. Flowers of plants of the new *Calylophus* are lighter yellow in color than flowers of plants of 'Southern Belle'.

Plants of the new *Calylophus* can also be compared to plants of *Oenothera hybrida* 'INNOENO131', disclosed in U.S. Plant Pat. No. 16,393. In side-by-side comparisons, plants of the new *Calylophus* differ primarily from plants of 'INNOENO131' in the following characteristics:

1. Leaves of plants of the new *Calylophus* have entire margins with shallow and widely-space serrations whereas leaves of plants of 'INNOENO131' are entire.
2. Plants of the new *Calylophus* have larger flowers than plants of 'INNOENO131'.
3. Flowers of plants of the new *Calylophus* are lighter yellow in color than flowers of plants of 'INNOENO131'.

BRIEF DESCRIPTION OF THE PHOTOGRAPHS

The accompanying colored photographs illustrate the overall appearance of the new *Calylophus* plant showing the colors as true as it is reasonably possible to obtain in colored reproductions of this type. Colors in the photographs may differ slightly from the color values cited in the detailed botanical description which accurately describe the colors of the new *Calylophus* plant.

The photograph on the first sheet (FIG. 1) is a side perspective view of a typical flowering plant of 'WNCYLALEM' grown in a container.

Figure 2:
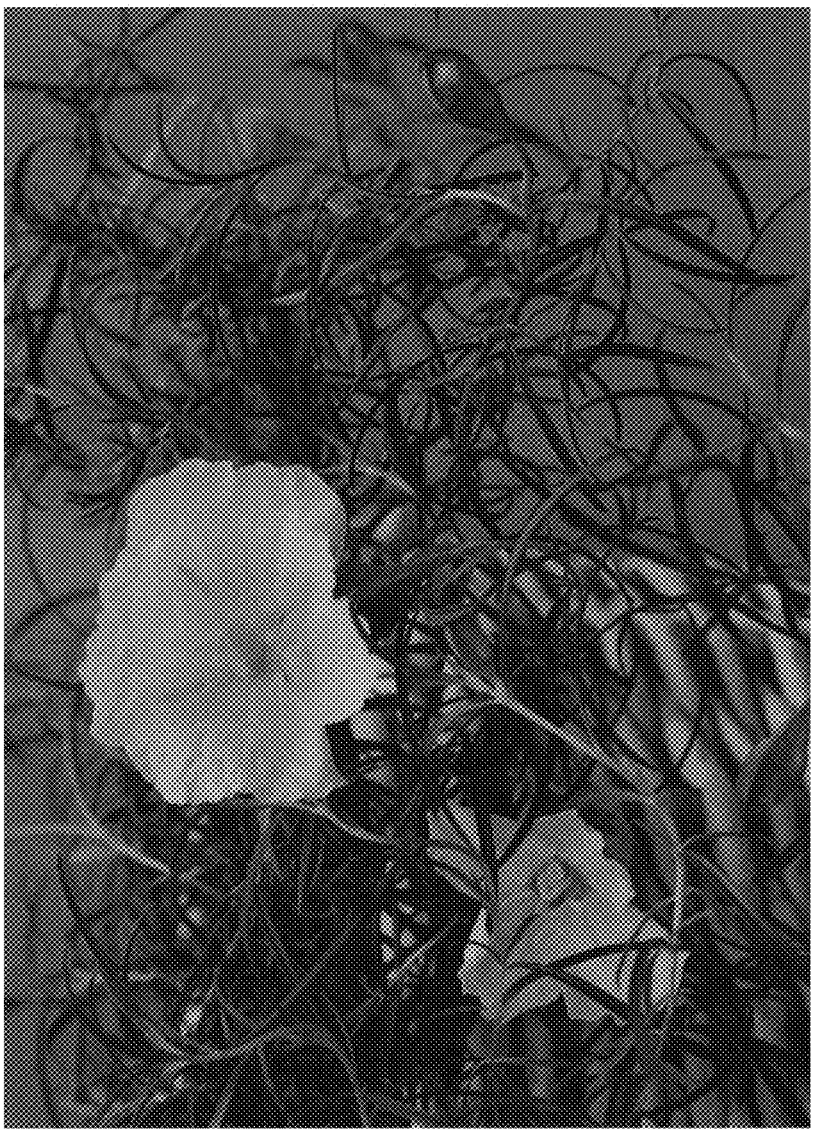

The photograph on the second sheet (FIG. 2) is a close-up view of a typical flowering plant of 'WNCYLALEM'.

DETAILED BOTANICAL DESCRIPTION

The aforementioned photographs and following observations and measurements describe plants grown during the late summer and early autumn in 10.8-cm containers in a corrugated polycarbonate-covered greenhouse in Carlton, Mich. and under cultural practices typical of commercial *Calylophus* production. During the production of the plants, day temperatures averaged 26° C., night temperatures averaged 20° C. and light levels averaged 9,290 foot-candles. Plants were pinched three weeks after planting and were ten weeks from planting rooted cuttings when the photographs and description were taken. In the following description, color references are made to The Royal Horticultural Society Colour Chart, 2015 Edition, except where general terms of ordinary dictionary significance are used.

Botanical classification: *Calylophus hybrida* 'WNCYLALEM'.

Parentage:

*Female, or seed, parent*.—Proprietary selection of *Calylophus hybrida* identified as code number 17TX073-02, not patented.

*Male, or pollen, parent*.—Proprietary selection of *Calylophus hybrida* identified as code number 17TX073-02, not patented.

Propagation:

*Type*.—Terminal vegetative cuttings.

*Time to initiate roots, summer*.—About ten days at soil temperatures about 24° C.

*Time to initiate roots, winter*.—About two weeks at soil temperatures about 18° C.

*Time to produce a rooted plant, summer*.—About four weeks at soil temperatures about 24° C.

*Time to produce a rooted plant, winter*.—About five weeks at soil temperatures about 18° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Outwardly spreading and mounding to eventually trailing and decumbent plant habit; lateral branches potentially developing at every node, dense and bushy plant form, pinching enhances development of lateral branches; moderately vigorous to vigorous growth habit and rapid growth rate; flowers held above and beyond foliar plane.

*Plant height*.—About 12 cm to 15 cm.

*Plant diameter* (*area of spread*).—About 46 cm to 61 cm.

*Lateral branches*.—Length: About 36 cm. Diameter: About 2 mm. Internode length: About 1.1 cm. Strength: Moderately strong; flexible, wiry. Aspect: Initially upright then outwardly spreading to trailing and decumbent. Texture and luster: Smooth, glabrous; slightly glossy. Color, developing and developed: Close to 144A to 144B variably tinged with close to 60A; with subsequent development, becoming woody, close to N199B to N199C.

Leaf description:

*Arrangement*.—Alternate; simple, sessile.

*Length*.—About 2.5 cm to 4.2 cm.

*Width*.—About 3 mm to 4 mm.

*Shape*.—Acicular; curled and reflexed.

*Apex*.—Acute to acuminate.

*Base*.—Cuneate to attenuate.

*Margin*.—Entire with shallow and widely-spaced serrations.

*Texture and luster, upper and lower surfaces*.—Smooth, glabrous; slightly; slightly glossy.

*Venation pattern*.—Pinnate; only midvein is readily visible.

*Color*.—Developing leaves, upper and lower surfaces: Close to 144A. Fully developed leaves, upper surface: Close to 147A; venation, close to 147A. Fully developed leaves, lower surface: Close to 147B; venation, close to 147B.

Flower description:

*Flower type and flowering habit*.—Single terminal and axillary rotate salverform flowers; flowers face mostly outwardly; freely flowering habit with flowers potentially forming at every node.

*Natural flowering season*.—Relatively long flowering period, plants flower from early spring into the autumn, flowering continuous during this period.

*Flower longevity on the plant*.—About two to three days; flowers not persistent.

*Fragrance*.—None detected.

*Flower buds*.—Length: About 1 cm. Diameter: About 8 mm. Shape: Roughly spherical, squarish. Texture and luster: Smooth, glabrous; slightly glossy. Color: Close to 144A and 144B.

*Flower diameter*.—About 4.2 cm.

*Flower depth* (*height*).—About 2 cm.

*Throat diameter*.—About 6 mm.

*Tube length*.—About 1.5 cm.

*Tube diameter, proximally*.—About 2 mm.

*Petals*.—Quantity and arrangement: Four petals fused in a single salverform whorl. Petal lobe length (from throat): About 1.8 cm. Petal lobe width: About 2 cm. Petal lobe shape: Spatulate with cordate tendencies. Petal lobe apex: Slightly retuse. Petal lobe margin: Entire to shallowly crenate; slightly undulate. Petal lobe texture and luster, upper surface: Smooth, glabrous; velvety; slightly glossy. Petal lobe texture and luster, lower surface: Smooth, glabrous; matte. Throat texture and luster: Smooth, glabrous; slightly glossy. Tube texture and luster: Smooth, glabrous; matte. Color: When opening and fully opened, upper surface: Close to 1C to 1D; towards the throat, close to 1A; venation, similar to lamina colors; colors do not change with subsequent development. When opening and fully opened, lower surface: Close to 1C; towards the tube, close to 1B to 1C; venation, similar to lamina colors; colors do not change with subsequent development. Flower throat (inside): Close to 1A; venation, close to 1A. Flower tube (outside): Close to 144B; venation, close to 144B.

*Sepals*.—Quantity and arrangement: Four sepals fused in a single whorl. Length: About 8 mm. Width: About 4.5 mm. Shape: Narrowly deltoid. Apex: Acute. Margin: Entire. Texture and luster, upper and lower surfaces: Smooth, glabrous; slightly glossy. Color: When opening and fully developed, upper surface: Close to 144B to 144C. When opening and fully developed, lower surface: Close to 144A to 144B.

*Peduncles*.—Length: About 1.2 cm. Width: About 2 mm. Strength: Strong; flexible, wiry. Angle: About 45° from stein axis. Texture and luster: Smooth, glabrous; slightly glossy. Color: Close to 146A.

*Reproductive organs*.—Stamens: Quantity per flower: About eight. Filament length: About 1.2 cm. Filament color: Close to 154D. Anther size: About 0.5 mm by 2 mm. Anther shape: Oblong. Anther color: Close to 154D. Pollen amount: Moderate to abundant. Pollen color: Close to 6A. Pistils: Quantity per flower: One. Pistil length: About 1.1 cm. Style length: About 1 cm. Style color: Close to 154D. Stigma diameter: About 2 mm. Stigma shape: Four-lobed. Stigma color: Close to 144B. Ovary color: Close to 144A to 144B.

*Seeds and fruits*.—To date, seed and fruit development has not been observed on plants of the new *Calylophus*.

Pathogen & pest resistance: To date, plants of the new *Calylophus* have not been noted to be resistant to pathogens or pests common to *Calylophus* plants.

Garden performance: Plants of the new *Calylophus* have been observed to have excellent garden performance and have been observed to tolerate rain, wind and temperatures ranging from about 1° C. to about 40° C.

It is claimed:

1. A new and distinct *Calylophus* plant named 'WNCYLALEM' as illustrated and described.

* * * * *